(12) United States Patent
Gaikar et al.

(10) Patent No.: US 6,365,601 B1
(45) Date of Patent: Apr. 2, 2002

(54) PROCESS FOR EXTRACTION OF PIPERINE FROM PIPER SPECIES

(75) Inventors: Vilas Gajanan Gaikar; Girija Raman, both of Mumbai (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 09/481,420

(22) Filed: Jan. 12, 2000

(30) Foreign Application Priority Data

Sep. 16, 1999 (IN) .................................................. 1238/99

(51) Int. Cl.⁷ ........................ A61K 31/47; A61K 35/78; A01N 43/42
(52) U.S. Cl. ........................ 514/315; 514/321; 546/397; 424/734
(58) Field of Search ................................ 514/315, 321; 546/397; 424/734

(56) References Cited

U.S. PATENT DOCUMENTS

| | | | |
|---|---|---|---|
| 4,138,212 A | | 2/1979 | Stransky |
| 5,210,316 A | | 5/1993 | Yang et al. |
| 5,536,506 A | * | 7/1996 | Majeed et al. |
| 6,054,585 A | * | 4/2000 | Majeed et al. |

OTHER PUBLICATIONS

Wood et al. Flavour Fragrance J. vol. 3, No. 2, pp. 55–64, abstract enclosed,1988.*

Borges et al. Nahrung. vol. 37, No. 2, pp. 127–130, abstract enclosed, 1993.*

Archer et al. J. Chromatogr. vol. 351, No. 3, pp. 595–598, abstract enclosed, 1986.*

The Condensed Chemical Dictionary, 10th ed., p. 547, 1981.*

Gromov, V., "Topochemistry of the Hydrotopic Delignification of Birch Wood," Khimiya Drevesiny, No. 15, pp. 16–26, BLL., English Abstract, 1974.

* cited by examiner

Primary Examiner—Christopher R. Tate
(74) Attorney, Agent, or Firm—Perkins Coie LLP (57) ABSTRACT

The present invention relates to a process for extraction of piperine of Formula I from the fruits of Piper species, comprising the steps of:

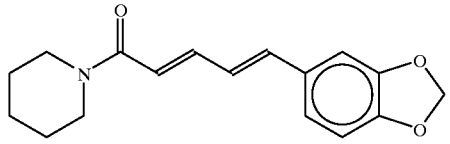

Formula 1 contacting the fruit of piper species with aqueous hydrotrope solution at a temperature in the range of 0–100° C. and separating the solution from the solid residue by known methods, and recovering piperine from the solution by known methods.

15 Claims, 4 Drawing Sheets

CROSS SECTION OF P. NIGRUM, NaCS SOAKED (DISTORTED)

Fig. 4

PROCESS FOR EXTRACTION OF PIPERINE FROM PIPER SPECIES

FIELD

The present invention relates to a process for extraction of piperine from Piper species such as *Piper nigrum, Piper retrofractum, Piper longum, Piper schmidtii*. This method is particularly related to the extraction of piperine using aqueous hydrotrope solutions for the first time.

BACKGROUND

Piperine ($C_{17}H_{19}O_3N$) is the major constituent of black pepper (*Piper nigrum*) and is used extensively as a spice, condiment, insecticide and for medicinal purposes. It has shown potent chemoprotective effect against procarcinogens (Reen and Rashmet, *J. Ethnopharmacol.*, 1997, 58(3), 165–173). The extracts of *Piper nigrum* are found to have a hypercoagulative effect in vitro., they lessen the clotting time by accelerating the thrombin activation and lowering the heparin level in the clotting systems. (Hasselstorm et.a)., *Food Res.*, 1954 19, 373). They are valued for their rubefacient properties and hence used as local application for sore throat, piles and some skin diseases (*Wealth of India, Raw Materials*, Vol.III, pg. 110).

The concentration of piperine is about 6% to 9% in *Piper nigrum*, 4.0% in *Piper longum* fruits and 4.5% in *Piper retrofractum*.

PRIOR ART FOR SEPARATION OF PIPERINE

H. Staudinger and H. Schnieider [Ber; 56, 699(1923)] described a process for the extraction of piperine from *Piper nigrum* fruits, wherein the alkaloid was extracted using ethanol and the extract was treated with aqueous sodium hydroxide to remove all the resinous matter. Other solvents used for extraction are petroleum ether and dichloromethane. The extraction of piperine into these organic solvents is not selective as other compounds like gums, polysaccharides and resins are extracted reducing the purity of piperine. The post extraction processing to purify piperine is cumbersome and uneconomical. A liquid pepper composition containing pepper in a concentrated form has been prepared by extracting the pepper fruits with acetone and subsequent treatment with anhydrous lactic acid (*Wealth of India, Raw Materials*, Vol. III, pg. 111).

Vidal, J. P. and Richard, H., (*Scientific Aliments* 1987, 7(3), 481–98) outlines a procedure for the production of black pepper oleoresins by dense carbon dioxide extraction or carbon dioxide+ethanol extraction. The extract contains 16.7% essential oils and 42.2% piperine which was very close to that obtained by dichloromethane as solvent.

Hans J. (3,706594 *German. Offen.* DE 28/02/1987, Beutler) described a process wherein gaseous carbon dioxide under supercritical conditions is passed downward through a packed bed of pulverised pepper and the loaded solvent is then expanded in a downstream separator for release of the extracted material. However, this process using supercritical fluid extraction is not economical and still a further solvent extraction step is essential for obtaining pure piperine.

Most of these prior art processes relate to the extraction of *Piper nigrum* oleoresin containing piperine and other volatile oils. Piperine containing oleoresin is then solvent extracted and recrystallised to obtain pure piperine. These conventional processes are carried out using a number of steps which often present difficult operating conditions and result in a high cost of production.

OBJECTS

The main object of the present invention is to provide a cost effective process for the extraction of piperine from Piper species in a substantially pure form using the phenomena of hydrotropy. The approach is to find a suitable hydrotrope for selective extraction of piperine from Piper species followed by dilution of the extract phase to precipitate piperine in pure form.

Another object is to provide a two step process for the selective extraction of phytochemicals like piperine exploiting the ability of hydrotropes to dissolve the otherwise water insoluble organic compounds in aqueous solution.

A further object is to provide a process for the recovery of piperine from the solution by simple dilution with water as most of the piperine precipitates out.

Still another object of the invention is to provide a process for the recovery of piperine from aqueous hydrotrope solution by extraction with organic solvents followed by de-solventisation.

Yet another object of the present invention is to provide a process for the extraction of piperine from *Piper nigrum* in the first step without using an organic solvent or excessive temperature to retain the purity of piperine.

SUMMARY

The invention provides a novel two-step process for the extraction of piperine from plants of piper species using aqueous hydrotrope solution.

DETAILED DESCRIPTION

Accordingly the present invention provides a process for extraction of piperine of Formula 1 from the fruit of Piper species comprises, said process comprising the steps of:

Formula 1 of Piperine (i) contacting the fruit of piper species with aqueous hydrotrope solution at a temperature in the range of 0–100° C. and separating the solution from the solid residue by known methods, and.

(ii) recovering the piperine from the solution obtained at the end of step (i) by known methods.

In an embodiment, piperine is recovered from the aqueous solution of hydrotrope obtained in step (i), after dilution with water so as to bring the concentration of hydrotrope sufficiently low to precipitate piperine from the solution in solid form and separating the precipitated piperine from the solution obtained, followed by washing with water or without dilution, by extraction with organic solvent selected from the group comprising aromatic hydrocarbons, aliphatic hydrocarbons, ethers, esters, ketones, amides, alcohols or mixtures thereof.

The General Process of the Invention is Described as Follows:

The dried fruits of Piper species such as *Piper nigrum, Piper longum, Piper retrofractum, Piper schmidtii* in pulverised form, preferably in the mesh size of 5 to 300 are brought in intimate contact with an aqueous solution of hydrotrope in the form of a slurry in a stirred vessel or in a column in which the coarse Piper species powder is packed and the solution passes over it. In the process of invention when the contacting is done in the stirred vessel the Piper species powder is added to the aqueous hydrotrope solution. After the aforementioned components are brought together, the mixture which is usually in the form of a slurry, is agitated for a period sufficient for the extraction of piperine to take place. A typical mixing time is in the range of 15 minutes to 24.00 hours depending upon the concentration of hydrotrope and the speed of agitation. The mixing is conducted at a selected temperature ranging from 0° C.–100° C. preferably at room temperature of 30° C. and atmospheric pressure.

The Plants of Piper species for the extraction of piperine is selected from the group comprising *Piper nigrum, Piper longum, Piper retrofractum, and Piper schmidtii.*

The term "hydrotrope" indicates short alkyl chain water soluble amphiphillic compounds. The hydrotrope is selected from the group comprising sodium, potassium, calcium, ammonium, magnesium salts of alkyl benzene sulfonates, such as benzene sulfonate, toluene sulfonate, xylene sulfonate, ethyl benzene sulfonate, styrene sulfonate, pseudocumene sulfonate, mesitylene sulfonate, propyl benzene sulfonate and butyl benzene sulfonate; alkyl polyglycol sulfates and phosphates such as methyl cellosolve sulfate, ethyl cellosolve sulfate, propyl cellosolve sulfate, butyl cellosolve sulfate, pentyl cellosolve sulfate, hexyl cellosolve sulfate and the corresponding phosphates with sodium, potassium, and calcium counterions; methyl diglycol sulfates, ethyl diglycol sulfates, propyl diglycol sulfates, butyl diglycol sulfates, pentyl diglycol sulfates, hexyl diglycol sulfates and phosphates salts of sodium, potassium, calcium and ammonium counterions; substituted aromatic carboxylates such as hydroxybenzotaes, toluates, chlorobenzoates, nitrobenzoates, alkyl benzene carboxylates with sodium, potassium, calcium and ammonium counterions; substituted phenates, such as hydroxyphenates, chlorophenates, alkyl phenates, naphthols; naphthalene carboxylates and substituted naphthalene carboxylates such as hydroxy naphthalene carboxylates.

After the mixing the solid residue is separated from the solution by decantation, filtration or centrifugation. The separated residue is washed with water and the washing is combined with filtrate or the filtrate is used as such for the recovery of piperine.

The filtrate is diluted with water to bring the concentration of hydrotrope low enough to precipitate piperine from the solution. The dilution is done at a temperature in the range of 0°–80° C. preferably in the range of 20°–30° C. The precipitated piperine is separated from the solution by decantation or filtration or centrifugation. The piperine is washed with water and dried. The hydrotrope solution recovered during this step is concentrated and recycled.

In another embodiment the filtrate obtained after the step (i) is subjected to extraction with an organic solvent for recovery of piperine from the aqueous solution of hydrotrope after dilution of the hydrotrope solution with water or without dilution. The organic solvent selected for the extraction should be immiscible with water and is selected from the group comprising aromatic hydrocarbons, aliphatic hydrocarbons, halogenated hydrocarbons, ethers, esters, alcohols, amides or mixtures thereof.

*Piper nigrum* fruits are small berries, sessile, globose, 6 mm. in diameter or less. They are spherical and have a deeply reticulated and coarsely wrinkled dark brown surface. At the apex, the remains of a sessile stigma are visible. The kernel consists almost entirely of perisperm, hollow at the centre surrounded by a scanty endosperm in which the minute embryo is embedded.

The epidermal cells consist of small rectangular cells, the hypodermis of thin walled parenchymatous cells and polygonal and rectangular stone cells. The inner epicarpic sclerenchyma consists of a single layer of brown lignified cells, starch in large polyhedral masses and oil cells of the perisperm and pericarp.

The cell wall of the *P. nigrum* fruits are made up of a cellulose crystallites which are elongated polyhedrons. They are present in an ordered manner and are not isodiametric. The cell wall as a whole is inhomogenous because on swelling with water it shows two phases. The fact that these cell walls can swell when soaked in water, and the return to their original dimensions explain the fact that they are not made up of single homogenous crystals. The plasma membrane of the cell is a phospholipid bilayer.

Figure 1:
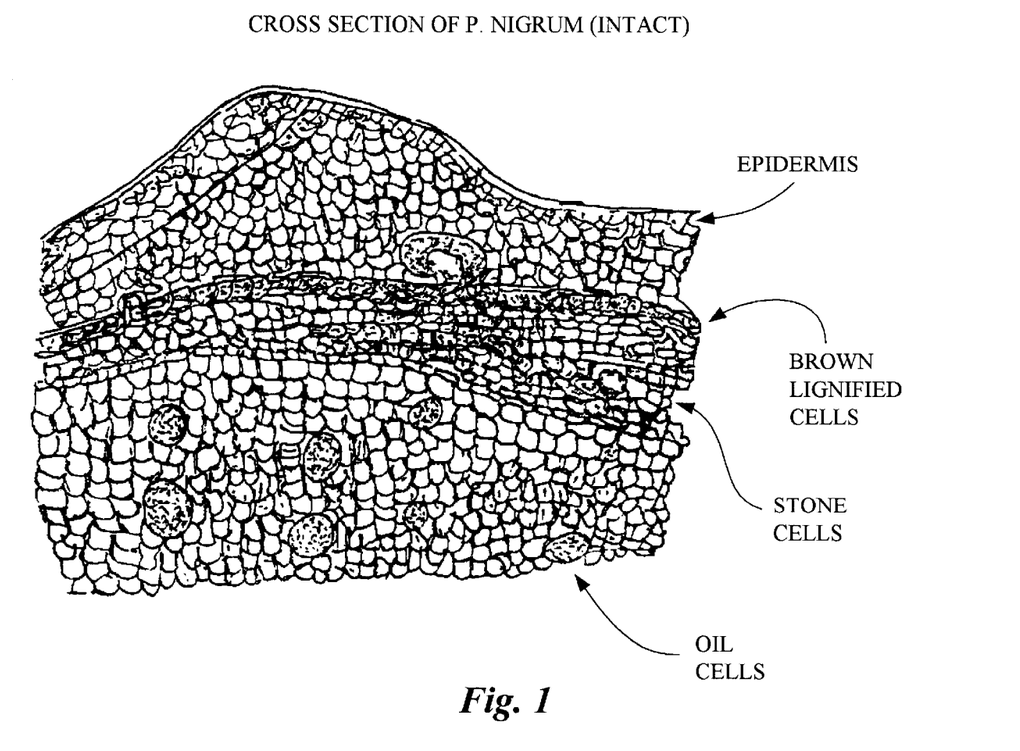
FIG. 1 represents microscopic transverse section of *P. nigrum* (intact).

This can be observed in the *P. nigrum* sections studied microscopically (FIG. 1). The pericarp, the epidermal cells and the other cellular consituents become turgid when they are soaked in water but the structure of the cells remains constant despite the water uptake.

Figure 2:
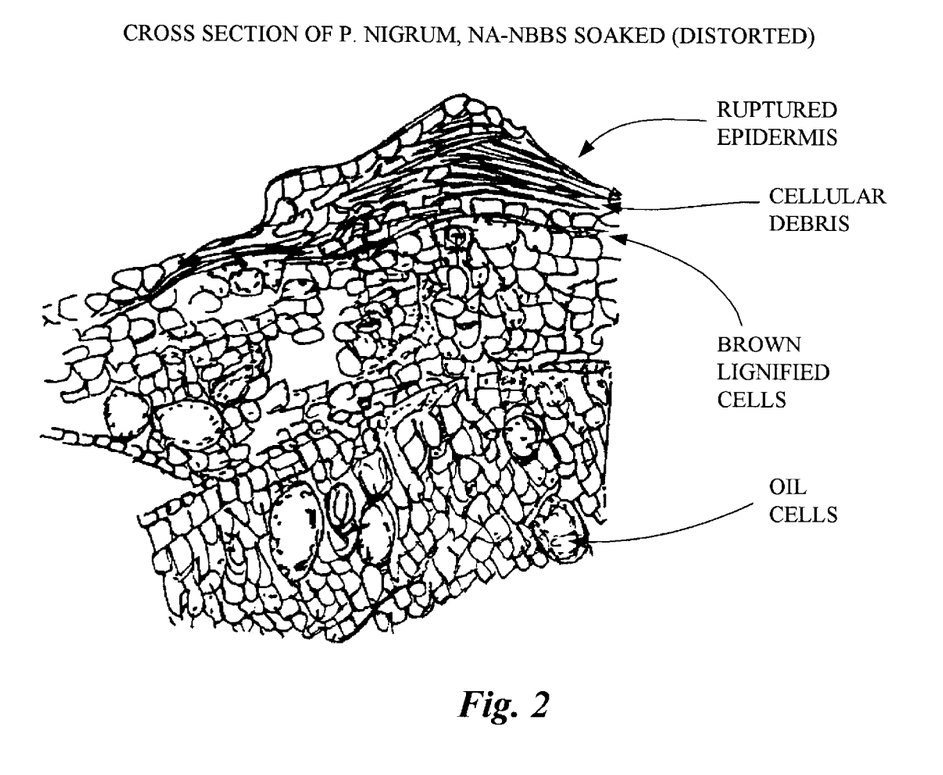
FIG. 2 represents section of *P. nigrum* taken after soaking pepper in hydrotrope solution; it shows destabilised epidermal cells.

From the *P. nigrum* sections taken after soaking whole pepper in different hydrotrope solutions, it is observed that the pericarp and the other epidermal layers are shattered and only cellular debris is present. In the case of N-butyl benzene sulfonate, the epidermal cells are destabilised and their polyhedral shapes have been distorted (FIG. 2). The hypodermal cells are more turgid and the intercellular space has increased. Thus, the cells are permeabilised and the extraction of piperine is facilitated. This epidermal permeabilisation can account for the excellent selectivity of extraction.

Figure 3:
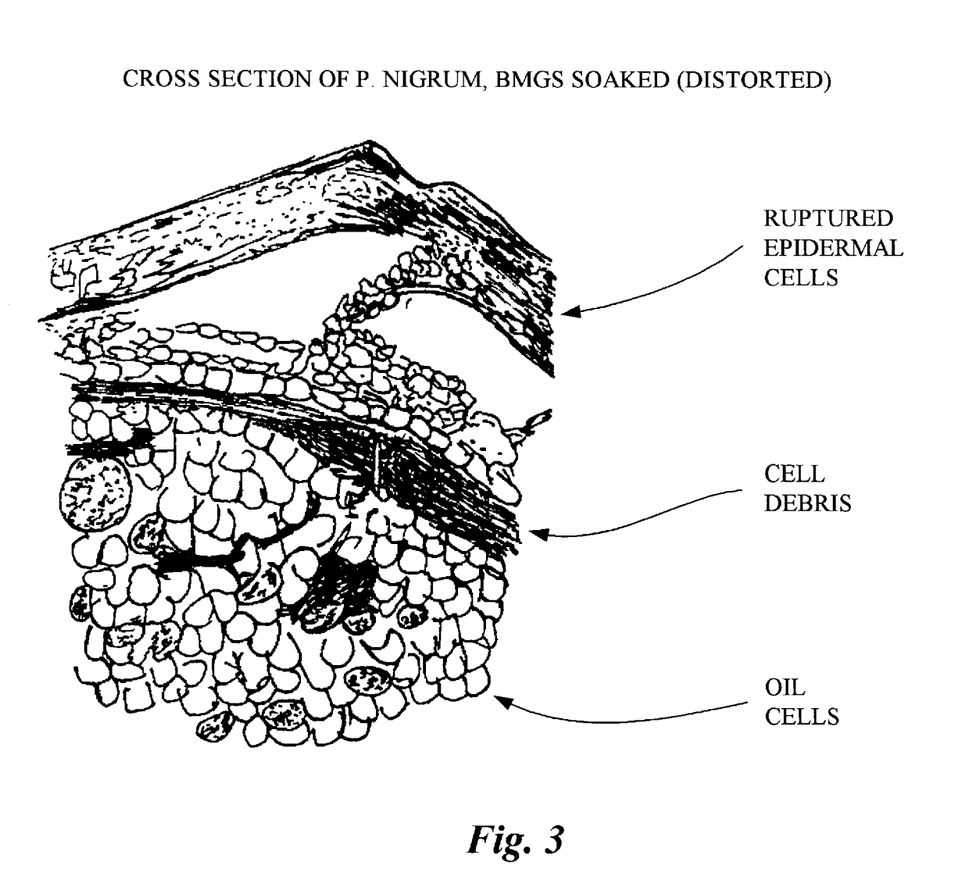
FIG. 3 represents a section of *P. nigrum* wherein the cellular layers are totally distorted due to permeation of N-butyl benzene sulfonate.

With N-butyl benzene sulfonate (Na NBBS) there is a total disordering of the cellular layers. The rectangular stone cells of the epicarp are slightly swollen but their structure is intact. This explains the high extraction efficiency and selectivity of Na NBBS for piperine (FIG. 3). The oil cells and the pericarp are very turgid after soaking in butyl mono glycol sulfate but their structure is intact. Thus, permeabilisation is facilitated which enhances selectivity of extraction.

Figure 4:
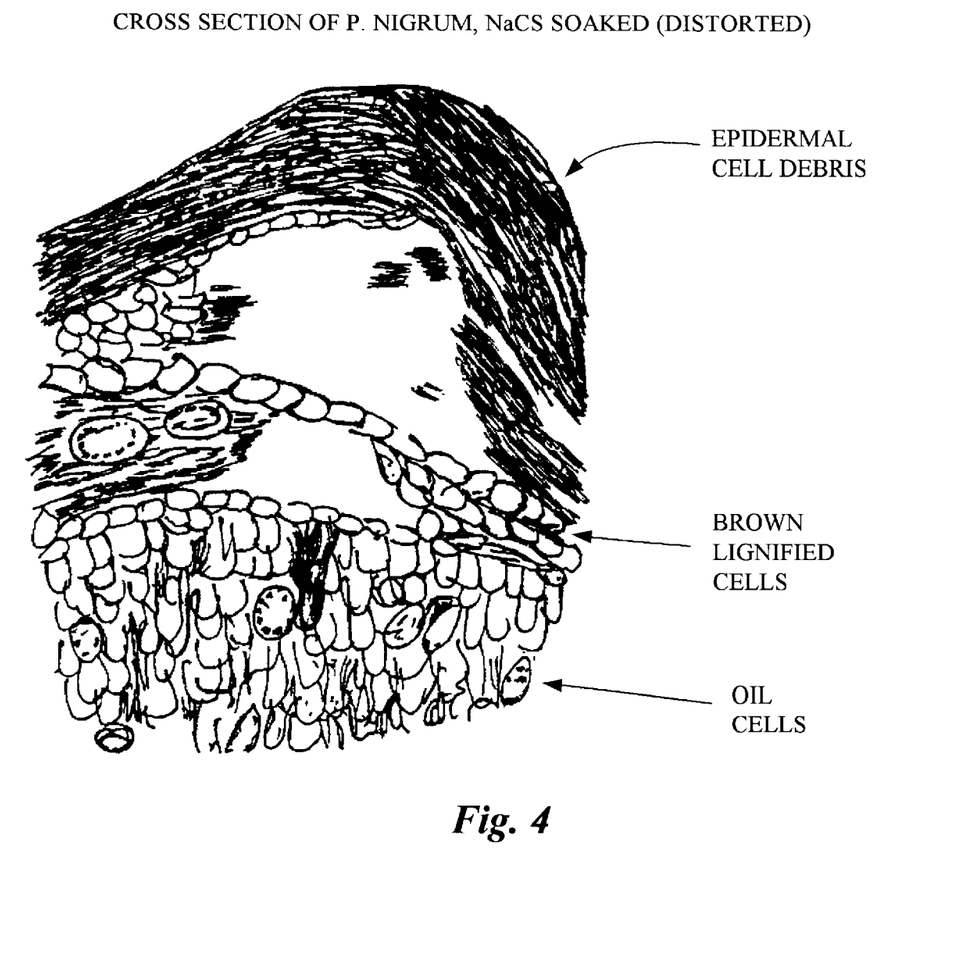
FIG. 4 represents a section of *P. nigrum* wherein the epidermal and hypodermal cells are disrupted and large holes are generated along with cell debris due to treatment with cumene sulphonate.

However, in the case of cumene sulphonate as the hydrotrope the entire layer of epidermal cells and hypodermal cells are disrupted and large holes are generated along with cell debris (FIG. 4). This can account for its lower selectivity of extraction of piperine.

Since extraction is carried out using pulverised raw material (mesh size # 6) there is a probability of the initial breakdown of the outer polysaccharide layers. This leaves the inner epicarp and epidermal layers open for hydrotrope attack. In order to get a more authentic picture of the penetration pattern of the hydrotrope, thin sections of *P. nigrum* were soaked in water and the hydrotrope solutions and studied microscopically.

Observations have been made before the after exposure of the cells to water and hydrotrope solutions. The cells after exposure to water become turgid but their cell structure remains intact. In the case of sodium xylene sulfonate the cells become more turgid and the inner cellular constituents are solubilised. However, the cell order remains intact like that of water. This can explain the low penetrability of sodium xylene sulfonate and subsequently its lower capacity for the extraction of piperine. In the case of sodium salt of p-toluene sulfonate the rupture of the hypodermal parenchymatous cells and brown lignified cells is seen but the epidermal cells seem to remain intact. This therefore accounts for its low extraction efficiency.

With sodium cemene sulfonate however, the total cellular nature is disrupted and there is a complete disordering of the cell layers. Only cellular debris epidermal region is visible along with a highly swollen and permeabilised layer of stone cells of the hypodermis. This explains the poor selectivity of extraction when this hydrotrope is used. With N-butyl benzene sulfonate (Na NBBS) there is a total disordering of the cellular layers especially the cells of the epicarp and the oil cells of the perisperm. The rectangular stone cells of the epicarp are slightly swollen but their structure is intact. This explains the high extraction efficiency and selectivity of Na NBBS for piperine. The cellular structure of the sections soaked in butyl mono glycol sulfate also show very turgid cells of the epicarp and oil cells of the perisperm but their shape remains intact and they are not distorted. Hence, the hydrotropic treatment increases the permeability for extraction and gives excellent selectivity for piperine but poor recovery.

The lysis of the cell wall is a process in which the hydrotrope is adsorbed on the membrane surface and penetrates into the membrane. It induces a change in the molecular organisation which alters the permeability of the membrance in such a fashion that the bioactive material piperine is released. The short bulky aromatic structure of the hydrotrope does not pack well in a lamellar liquid crystalline structure of the cell wall. The lamellar structure of the cell wall is destabilised by the hydrotrope solution and there is a considerable increase in the solubility of the hydrophobic moiety beyond a minimum hydrotrope concentration of the hydrotrope which is a characteristic of a hydrotrope. Beyond this value hydrotropes form microassemblies which trap the hydrophobic piperine which is released in solution due to cell wall rupture. This combined mechanism of cell rupture and solubilisaiton has been uniquely used for the extraction of piperine from *Piper nigrum*.

The objects of the invention, its advantages and means of attaining the same are disclosed hereunder in greater detail with reference to the non-limiting exemplary embodiments of the same. The examples are by way of illustration only and in no way restrict the scope of the invention.

Chemicals Used

*Piper nigrum* (Dried fruits of black pepper)
Sodium butyl glycol sulphate (50% aqueous solution, Hulls Germany)
Sodium n-butyl benzene sulphonate salt (synthesised in the laboratory)
Sodium cumene sulphonate (Navdeep Chemicals Pvt.Ltd.)
Sodium xylene sulphonate (Navdeep Chemicals Pvt.Ltd.)
Sodium p-toluene sulphonate(Navdeep Chemicals Pvt.Ltd)
Dichloromethane (AR grade)
Methanol (HPLC grade)
Method of Analysis: High Performance Liquid Chromatography with $C_{18}$ reverse phase column.

EXAMPLE 1

Whole pepper 20 gms was pulverised to a coarse powder of mesh size# 6 and was added to 100 ml aqueous sodium butyl glycol sulfate of 2.5 gmol/lit concentration and the suspension was stirred vigorously for 2 hours at 30° C. The solution was filtered and then diluted by addition of 310 ml waterThe precipitated piperine was dried and analysed for purity. The recovery of piperine was 58.8% (716 mg.) based on the amount of piperine present in the dried fruit with a purity of 98%.

EXAMPLE 2

Whole pepper 20 gms was pulverised to a coarse powder of mesh size# 6 and added to 100 ml aqueous sodium butyl glycol sulfate 2.5 of gmol/lit concentration and the suspension was stirred vigorously for 2 hours at 80° C. The solution was filtered and then diluted three times by addition of 310 ml water. The precipitated piperine was dried and then dissolved in dichloromethane and analysed for purity. The recovery of piperine was 56.38% (687 mg.) based on the amount of piperine present in the dried fruit with a purity of 89%.

EXAMPLE 3

Whole pepper 20 gms was pulverised to a coarse powder of mesh size# 6 and added to 100 ml aqueous sodium n-butyl benzene sulfonate of 1.0 gmol/lit concentration and the suspension was stirred vigorously for 2 hours at 30° C. The solution was filtered and then diluted by the addition of 2000 ml of water. The precipitated piperine was separated by centrifugation, dried and then dissolved in dichloromethane and analysed for purity. The recovery of piperine was 63.92% (0.76 g.) based on the amount of piperine present in the dried fruit with a purity of 97.4%.

EXAMPLE 4

Whole pepper 20 gms was pulverised to a coarse powder of mesh size# 6 and added to 100 ml aqueous sodium n-butyl benzene sulfonate of 2.0 gmol/lit concentration and the suspension was stirred vigorously for 2 hours at 30° C. The solution was filtered and then diluted by addition of 2000 ml. of water. The precipitated piperine was separated by centrifugation, dried and then dissolved in dichloromethane and analysed for purity. The recovery of piperine was 95.75% (1.14 g.) based on the amount of piperine present in the dried fruit with a purity of 93%.

EXAMPLE 5

Whole pepper 20 gms was pulverised to a coarse powder of mesh size# 72 and added to 100 ml aqueous sodium n-butyl benzene sulfonate of 2.0 gmol/lit concentration and the suspension was stirred vigorously for 2 hours at 30° C. The solution was filtered and then diluted by addition of 2000 ml of water. The precipitated piperine was separated by centrifugation, dried and then dissolved in dichloromethane and analysed for purity. The recovery of piperine was 92.14% (1.095 g.) based on the amount of piperine present in the dried fruit with a purity of 90.15%.

EXAMPLE 6

Whole pepper 20 gms was pulverised to a coarse powder of mesh size #300 and added to 100 ml aqueous sodium n-butyl benzene sulfonate 2.0 gmol/lit concentration and the suspension was stirred vigorously for 2 hours at 30° C. The solution was filtered and then diluted by addition of 2000 ml water. The precipitated piperine was separated by centrifugation, dried and then dissolved in dichloromethane and analysed for purity. The recovery of piperine was 90.14% (1.07 g.) based on the amount of piperine present in the dried fruit with a purity of 89.14%.

EXAMPLE 7

Whole pepper 20 gms was pulverised to a coarse powder of mesh size# 6 and was added to 100 ml aqueous sodium n-butyl benzene sulfonate of 2.0 gmol/lit concentration and was stirred vigorously for 2 hours at 30° C. The solution was filtered and then extracted with 50 ml. dichloromethane three times. The recovered piperine was analysed for purity. The recovery of piperine was 96.82% (1.15 g.) based on the amount of piperine present in the dried fruit with a purity of 95.13%.

EXAMPLE 8

Whole pepper 20 gms was pulverised to a coarse powder of mesh size# 6 and added to 100 ml of aqueous sodium xylene sulfonate 2.0 gmol/lit concentration and was stirred vigorously for 2 hours at 30° C. The solution was filtered and then diluted by addition of 2000 ml water. The precipitated piperine was separated by centrifugation, dried and then dissolved in dichloromethane and analysed for purity. The recovery of piperine was 65.43% (0.77 g.) based on the amount of piperine present in the dried fruit with a purity of 60.41%.

EXAMPLE 9

Whole pepper 20 gms was pulverised to a coarse powder of mesh size# 6 and added to 100 ml of aqueous sodium cumene sulfonate 2.0 gmol/lit concentration and was stirred vigorously for 2 hours at 30° C. The solution was filtered and then diluted by addition of 2000 ml water. The precipitated piperine was separated by centrifugation, dried and then dissolved in dichloromethane and analysed for purity. The recovery of piperine was 72.3% (0.85 g.) based on the amount of piperine present in the dried fruit with a purity of 68.00%.

EXAMPLE 10

Whole pepper 20 gms was pulverised to a coarse powder of mesh size# 6 and added to 100 ml aqueous sodium p-toluene sulfonate of 2.0 gmol/lit concentration and the suspension was stirred vigorously for 2 hours at 30° C. The solution was filtered and then diluted by addition of 2000 ml water. The precipitated piperine was separated by centrifugation, dried and then dissolved in dichloromethane and analysed for purity. The recovery of piperine was 49% (0.582 g.) based on the amount of piperine present in the dried fruit with a purity of 52.3%.

A table giving the hydrotropes used in respect of plant materials and how they affected the respective yield of the extracts.

TABLE 1

Different hydrotropes used for extraction

| Hydrotrope (Sodium Salts) | Piperine | |
|---|---|---|
| | % Extraction | % Purity |
| Butyl mono glycol sulfate (Na-BMGS) | 58.8 | 98.0 |
| N-butyl benzene sulfonate (Na-NBBS) | 95.75 | 93.0 |
| Cumene sulfonate (Na-CS) | 72.3 | 68.0 |
| Xylene sulfonate (Na-XS) | 65.43 | 60.41 |
| p-Toluene sulfonate | 49.0 | 52.3 |

In the case of extraction of piperine from *Piper nigrum*, Na-BMGS gives less extraction but a very high selectivity. It is also observed that amongst the alkyl benzene sulfonates, butyl benzene derivatives show a much better extraction efficiency as compared to that of other hydrotropes.

The main advantages of the present invention are

1. A simple practically viable method has been provided for the extraction of piperine.
2. The number of steps required for extraction have been reduced and simple operating conditions are provided which can reduce the cost of production.
3. The hydrotrope solution can be recycled with or without the concentration step for further extraction which reduces the cost of chemicals.
4. The process of the present invention is carried out preferentially at lower temperature which is an improvement over the prior art as it does not degrade piperine and other chemicals.
5. The first step of the process of the present invention is carried out without the use of any organic solvent, which retains the purity of piperine and is an improvement over the prior art.

What is claimed is:

1. A process for extraction of piperine of formula shown below from the fruits of Piper species comprising the steps of:
   (i) contacting the fruit of Piper species with aqueous hydrotrope solution at a temperature in the range of 0–100° C., wherein the hydrotrope is selected from a group consisting of alkali metal salts of alkyl benzene sulfonates, alkyl polyglycol sulfates or phosphates, substituted aromatic carboxylates, substituted phenates, substituted naphthonates, substituted naphthalene carboxylates and alkali metal saccharines;
   (ii) separating the solution from the solid residue; and
   (iii) recovering piperine from the solution by a method selected from a group consisting of dilution and solvent extraction.

2. A process as claimed in claim 1 wherein the fruit obtained from a plant of Piper species used in the step (i) is selected from *Piper nigrum, Piper longrum, Piper retrofactum, Piper schmidtii*.

3. A process as claimed in claim 1 wherein the alkali metal salts of alkyl benzene sulfonates are selected from sodium, potassium, calcium, magnesium and ammonium salts of alkyl benzene sulfonates.

4. A process as claimed in claim 1 wherein the alkyl benzene sulfonates are selected from the group comprising benzene sulfonate, toluene sulfonate, xylene sulfonate, ethyl benzene sulfonate, styrene sulfonate, pseudocumene sulfonate, mesitylene sulfonate, propyl benzene sulfonate and butyl benzene sulfonate.

5. A process as claimed in claim 1 wherein the alkyl polyglycol sulfates and phosphates are selected from the group comprising methyl cellosolve sulfate, ethyl cellosolve sulfate, propyl cellosolve sulfate, butyl cellosolve sulfate, pentyl cellosolve sulfate, hexyl cellosolve sulfate and the corresponding phosphates containing sodium, potassium, and calcium counterions, methyl diglycol sulfates, ethyl diglycol sulfates, propyl diglycol sulfates, butyl diglycol sulfates, pentyl diglycol sulfates, hexyl diglycol sulfates and phosphate salts of sodium, potassium, calcium and ammonium counterions.

6. A process as claimed in claim 1 wherein the substituted aromatic carboxylates are selected from the group comprising hydroxybenzotaes, toluates, chlorobenzoates, nitrobenzoates, alkyl benzene carboxylates with sodium, potassium, calcium and ammonium counterions.

7. A process as claimed in claim 1 wherein the substituted phenates are selected from the group comprising hydroxyphenates, chlorophenates, alkyl phenates and naphthols.

8. A process as claimed in claim 1 wherein the substituted naphthalene carboxylates are selected from the group comprising hydroxy naphthalene carboxylates.

9. A process as claimed in claim 1 wherein the solvent in the extraction method is selected from the group of organic solvents comprising aliphatic hydrocarbons, aromatic hydrocarbons, ketones, esters, ethers, alcohols, amides or mixtures thereof.

10. A process as claimed in claim 1 wherein the dilution method for recovery of piperine from the solution comprises addition of water in an amount sufficient to lower the concentration of the hydrotrope solution and effect precipitation of piperine from the solution, and the precipitate is separated by filtration, centrifugation or decantation.

11. A process as claimed in claim 1 wherein the dilution is effected at the temperature in the range 0° C. to 80° C.

12. A process as claimed in claim 1 wherein the solvent extraction method comprises addition of organic solvent to the solution.

13. A process as claimed in claim 1 wherein dried fruit of Piper species are pulverised at the beginning of step (i) in mesh size in the range of 5 to 300.

14. A process as claimed in claim 13 wherein the pulverised dried Piper fruits and aqueous hydrotrope solution is agitated for a period of 15 minutes to 24 hrs at a temperature in the range of 0° C. to 100° C.

15. A process as claimed in claim 1 wherein the dilution is effected at the temperature in the range 20 C to 30 C.

* * * * *

UNITED STATES PATENT AND TRADEMARK OFFICE
CERTIFICATE OF CORRECTION

PATENT NO.    : 6,365,601 B1
DATED         : April 2, 2002
INVENTOR(S)   : Gaikar et al.

It is certified that error appears in the above-identified patent and that said Letters Patent is hereby corrected as shown below:

Column 1,
Line 21, ")" should be -- I --;
Line 31, "Schnieider" should be -- Schneider --;

Column 6,
Line 15, insert period between "water" and "The";

Column 8,
Line 64, "longrum" should be -- longum --;

Signed and Sealed this

Eighteenth Day of June, 2002

Attest:

Attesting Officer

JAMES E. ROGAN
*Director of the United States Patent and Trademark Office*